United States Patent
Del Soldato (12)

(10) Patent No.: US 6,645,965 B1
(45) Date of Patent: Nov. 11, 2003

(54) NITRATE SALTS OF ANTIHYPERTENSIVE MEDICINES

(75) Inventor: Piero Del Soldato, Milan (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 09/719,164

(22) PCT Filed: Jun. 15, 1999

(86) PCT No.: PCT/EP99/04138

§ 371 (c)(1),
(2), (4) Date: Dec. 12, 2000

(87) PCT Pub. No.: WO99/67231

PCT Pub. Date: Dec. 29, 1999

(30) Foreign Application Priority Data

Jun. 19, 1998 (IT) ............................................ MI98A1408

(51) Int. Cl.[7] ..................... A61K 31/519; C07D 487/04
(52) U.S. Cl. ............... 514/248; 514/252.16; 514/261.1; 514/275; 544/237; 544/254; 544/262; 544/322; 544/323
(58) Field of Search ................................ 544/237, 254, 544/262, 322, 323; 514/248, 252.16, 261.1, 275

(56) References Cited

U.S. PATENT DOCUMENTS 5,250,534 A * 10/1993 Bell et al. .................... 514/258
5,958,926 A * 9/1999 Garvey et al. ............... 514/253

FOREIGN PATENT DOCUMENTS

EP  0 759 899 B1  9/1999

OTHER PUBLICATIONS

Remington's Pharmaceutical Sciences, Gennaro et al, 15th Ed., 1975.
"The Anesthetized Guinea Pig as a Versatile Pharmacological Test Object", Journal of Pharmacological Methods 5, Del Soldato et al, 1981, pp 279–285.
"Pharmacological Characterization of Purinergic Receptors in the Rat Vas Deferens", The Journal of Pharmacology and Experimental Therapeutics, Taylor et al, vol. 224, No. 1, 1983, pp. 40–45.
"Chronic Inhibition of Nitric Oxide Synthesis—A New Model of Arterial Hypertension",Hypertension, Ribeiro et al, vol. 20, 1992, pp. 298–303.
"Non–synergistic relaxant effects of vasoactive intestinal polypeptide and SIN–1 in human isolated cavernous artery and corpus cavernosum", European Journal of Pharmacology, Hempelmann et al, vol. 276, 1995, pp. 277–280.
"Nonpeptide Angiotensin II Receptor Antagonists IV. EXP6155 and EXP6803", Hypertension, Wong et al, vol. 13, 1989, pp 489–497.
"Action of Beta–Adrenolytics on the Isolated Guinea–Pig Atria", Arch. Int. Pharmacodyn., Grodzinska et al, vol. 191, 1971, pp. 133–141.
"Selective cyclo–oxygenase–2 inhibitors and their influence on the protective effect of a mild irritant in the rat stomach", British Journal of Pharmacology, Gretzer et al, vol. 123, 1998, pp. 927–935.

* cited by examiner

*Primary Examiner*—Richard L. Raymond
(74) *Attorney, Agent, or Firm*—Arent Fox Kintner Plotkin & Kahn PLLC

(57) ABSTRACT

Nitric acid salts with medicines having an antihypertensive activity.

8 Claims, No Drawings

NITRATE SALTS OF ANTIHYPERTENSIVE MEDICINES

This application is a 371 application of International Application Number PCT/EP99/04138, filed Jun. 15, 1999.

The present invention relates to compounds and their compositions to be used in the hypertension therapy and prophylaxis. More specifically it relates to the use of said hypertensives for systemic and local use, in particular for the cardiovascular area. More specifically the present invention relates to new antihypertensive compounds having an improved performance.

The known compounds of the prior art used in the hypertension treatment generally have a limited efficacy. The hypertension treatment is usually carried out by administering to the patient the antihypertensives in association with other medicines active on the vascular system, such as for instance calcium-antagonists, diuretics, beta-blockers, ACE inhibitors. For example the antihypertensive antagonists of the angiotensin (ex. Losartan), the calcium antagonists (ex. dihydropyridines), diuretics (for example thiazidic derivatives, direct and undirect vasodilators (ex. Minoxidil, Zaprinast) are not able when used alone to assure the therapy success.

It is necessary moreover to point out that some antihypertensives cause side effects for the respiratory apparatus, such as bronchoconstriction, dyspnea. For instance the antihypertensive used in the angina pectoris and cardiac arrhythmias treatment, for instance Timolol and Propanolol, give said side effects.

Other antihypertensives induce vasodilatation through phosphodiesterases inhibition and show side effects for various apparatuses (gastrointestinal, cardiovascular, ocular, etc.) See for instance Sildenafil and Zaprinast.

The need was felt to have available compositions active in the hypertension pathology treatment for systemic and local use, in particular of the cardiovascular area, with improved therapeutic profile. In particular the need was felt, moreover, to have available antihypertensive medicines having a beta-blocking or antiphosphodiesterasic action with lower side effects.

The Applicant has unexpectedly and surprisingly found compounds and pharmaceutical compositions usable in the treatment of the hypertension pathologies for systemic and local use, particularly of the cardiovascular area, with improved therapeutic profile, and without the side effects of the known hypertensive medicines.

It is an object of the present invention nitrate salts of compounds having an antihypertensive activity, or pharmaceutical compositions thereof, for systemic and local use, particularly to be used for the cardiovascular area, said compounds being characterized in that they contain least a reactive group capable to be salified, said compounds being selected from the following classes:

Class (A1b):

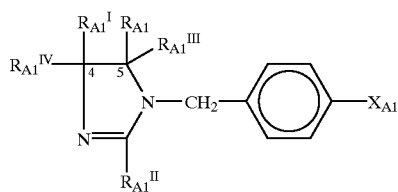
(A1b)

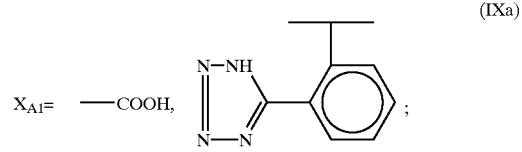
(IXa)

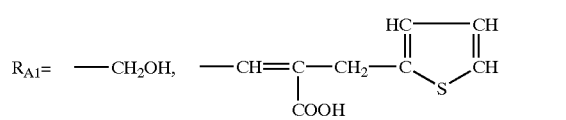
(IXb)

$R_{A1}$=—O with $R^{III}_{A1}$ free valence, so as to form in combination with the carbon atom in 5 position a ketone group, $R_{A1}$ together with $R^{I}_{A1}$ and the carbon atoms in 4 and 5 position of the heterocyclic ring in the compound of formula (A1b), with $R^{IV}_{A1}$ and $R^{III}_{A1}$ free valences, forms the aromatic ring having 6 carbon atoms containing a —COOH group:

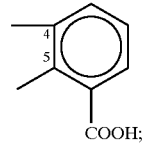
(IXc)

$R^{I}_{A1}$=H, Cl;

$R^{I}_{A1}$ with $R_{A1}$, $R^{IV}_{A1}$, $R^{III}_{A1}$ and the carbon atoms in 4 and 5 position of the heterocyclic ring of formula (A1b) forms the aromatic ring containing a COOH group (IXc), $R^{I}_{A1}$ with $R^{IV}_{A1}$ and with the carbon atom in 4 position of the heterocyclic ring of formula (A1b) forms the following saturated ring having five carbon atoms:

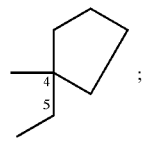
(IXd)

$R^{II}_{A1}$=—(CH$_2$)$_3$—CH$_3$, —O—CH$_2$—CH$_3$;

$R^{III}_{A1}$=H, free valence, $R^{III}_{A1}$ free valence with $R^{IV}_{A1}$ free valence forms a double bond between the carbon atoms in 4 and 5 position in the heterocyclic ring of formula (A1b), $R^{III}_{A1}$ with $R^{IV}_{A1}$, $R^{IV}_{A1}$ and the carbon atoms in 4 and 5 position of the heterocyclic ring of formula (A1b) forms the aromatic ring containing a —COOH group (IXc);

$R^{IV}_{A1}$=free valence, $R^{IV}_{A1}$ along with $R^{I}_{A1}$ with the carbon atom in 4 position of the heterocyclic ring of formula (A1b) forms the saturated ring having five carbon atoms (IXd)

$R^{IV}_{A1}$ with $R^{III}_{A1}$, $R^{I}_{A1}$ and the carbon atoms in 4 and 5 position of the heterocyclic ring of formula (A1b) forms the aromatic ring containing a —COOH group (IXc), $R^{IV}_{A1}$ with $R^{III}_{A1}$ both free valences form a double bond between the carbon atoms in 4 and 5 position of the heterocyclic ring of formula (A1b);

Class (A1c):

(A1c)

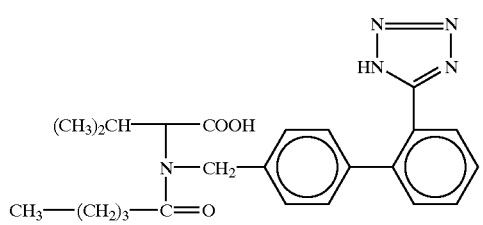

known as Valsartan;

Class (A2):

the precursors of this class are the following ones: 1 (2H)-phthalazinone hydrazone (Hydralazine); 6-(1-piperidiny-1)-2,4-pyrimidinediamine 3-oxide (Minoxidil); 1-[[3-(4,7-dihydro-1-methyl-7-oxo-3-propyl-1H-pyrazol [4,3-d]pyrimidin-5-yl)-4-etoxyphenyl]sulphonyl]-4-methyl-piperazine (Sildenafil), 2-(2-propyloxyphenyl)-8-azapurin-6-one (Zaprinast);

Class (A3):

(A3)

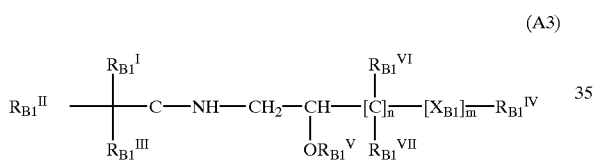

$R^{I}_{B1}$ and $R^{II}_{B1}$, equal to or different from each other, are H, CH$_3$, (XIa)

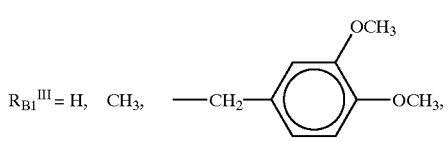

(XIb)

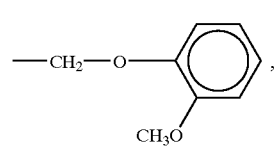

(XIc)

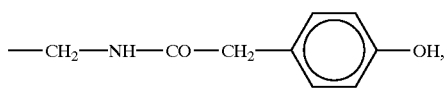

(XId)

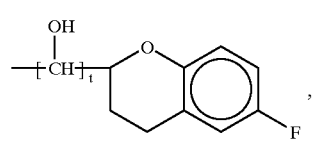

(XIe)

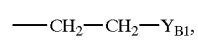

In the formula (XId) t=0, 1.

In the formula (XIe) $YB_{B1}$ can have the following meanings:

(XIf)

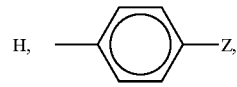

in the formula (XIf) Z=H, —OCH$_3$;
in the formula (A3):
$X^{IB}_1$=—O—, —S—;
n and m, equal to or different from each other, are 0, 1;

(XIh)

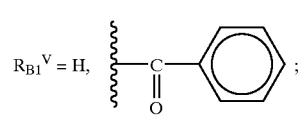

(XIg)

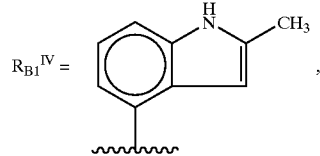

(XIi)

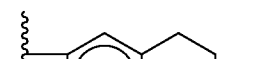

(XIm)

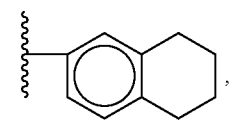

(XIn)

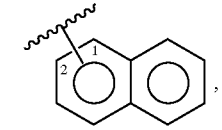

(XIo)

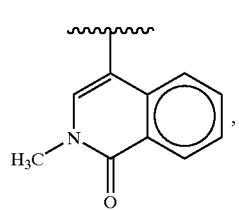

(XIr)

—CH$_2$—CH(OH)—CH$_2$—NH—CH(CH$_3$)$_2$, (XIp)

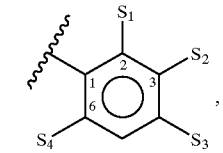

(XIs)

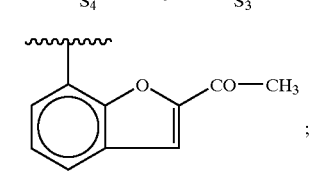

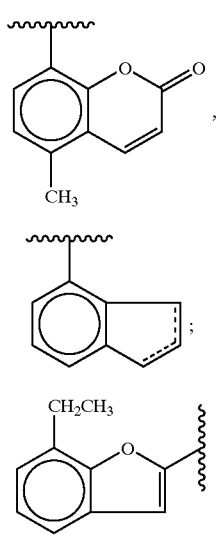

in the formula (XIp):

$S_1$=H, CN, OCH$_3$, CH$_3$, —CH$_2$—CH$_3$, —O—CH$_2$—CONH—CH$_3$, —COCH$_3$, —CO—(CH$_2$)$_2$—CH$_3$, —O—CH$_2$—CH=CH$_2$, —CH$_2$—CH=CH$_2$, cyclopentyl, or

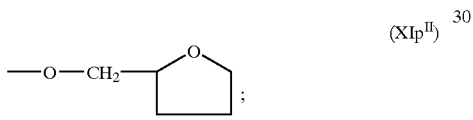

$S_2$=H, CH$_3$, Cl, —SOCH$_3$, —CONH$_2$;

$S_1$ with $S_2$ and the carbon atoms in 2 and 3 position of the C$_6$ aromatic ring of the same radical (XIp) forms the following ring:

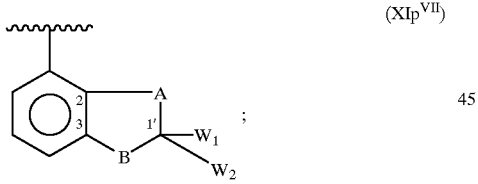

wherein:

[$^{(*)}$ atom adjacent to the aromatic ring of the formula XIp$^{VII}$]

B=—CH$_2$—, —NH—, —CH=CH—, $^{(*)}$—CO—CH$_2$—;
A=—O—, $^{(*)}$—CH$_2$—CH(OH)—, $^{(*)}$—O—CH$_2$—, $^{(*)}$—S—CH$_2$—, —CH$_2$—CH$_2$—, —CH$_2$—,

A is a tertiary carbon atom and contemporaneously W1 is free valence so as to form a double bond —CH=CH— between A and the carbon atom in 1' position, A in the ring having 5 atoms (XIp$^{VII}$) is a tertiary carbon atom containing a substituent such that with the carbon atom in 1' position and with one of the two W1 or W2 radicals, the other radical being free valence, forms an aromatic ring having 6 carbon atoms according to the following formula:

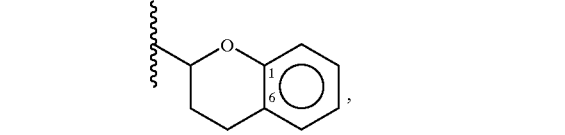

W1=H, free valence, when W1 is free valence and A is a tertiary carbon atom as above defined, a double bond between A and the carbon atom in 1' position is formed, W1 together with W2, the carbon atom in 1' position and the substituent A forms an aromatic ring having 6 carbon atoms;

W2=free valence, H, OH, —CH$_3$, —ONO$_2$, —O which with W1=free valence and the carbon atom in 1' position forms a ketone group, W2 together with W1, the carbon atom in 1' position and the substituent A forms an aromatic ring having 6 carbon atoms; $S_3$=H, F, Cl, OH, NO$_2$,—CH$_2$—CO—NH$_2$—(CH$_2$)$_2$—OCH$_3$, —NH—COCH$_3$, —CH$_2$—O—CH$_2$—CH$_2$—O—CH(CH$_3$)$_2$, —CH$_2$—CH$_2$—COOCH$_3$, —NH—CO—N(C$_2$H$_5$)$_2$, —NH—CO—(CH$_2$)$_2$—CH$_3$, —NH—SO$_2$—CH$_3$—NH—CO—NH—[cyclohexyl], —CH$_2$—CH$_2$—O—CH$_2$—[cyclopropyl];

$S_4$=H, Cl, —CH$_2$—CH$_2$— which with the carbon atoms in 1 and 6 position of the aromatic ring of the same radical (XIp) and with $X_{B1}$ in the formula (A3) equal to oxygen, being contemporaneously m n=1 and $R^{VII}_{B1}$ free valence, forms the following ring:

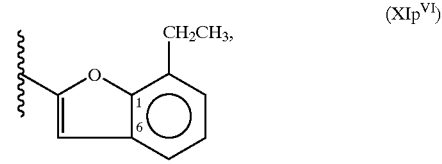

$S_4$ is a tertiary carbon atom which with the carbon atoms in 1 and 6 position of the aromatic ring of the radical (XIp), and with the following components of the formula (A3): the carbon atom —|C|$_n$—(n=1), the radical $X_{B1}$ equal to oxygen (m=1), and $R^{VII}_{B1}$ with $R^{V1}_{B1}$ free valences, forms the following ring:

(XIp$^{VI}$)

$R^{VI}_{B1}$=H, free valence;
$R^{VII}_{B1}$=H, free valence;

Other compounds belonging to this class are the following: 2-hydroxy-5-[1-hydroxy-2-[(1-methyl-3-phenylpropyl)amino]ethyl] benzamide (Labetalol), 1-(4-amino-6,7-dimethoxy-2-quinazolinyl)-4-[(tetrahydro-2-furanyl)carbonyl] piperazine (Terazosin), 1-(4-amino-6,7-dimethoxy-2-quinazolinyl)-4-(2-furanylcarbonyl) piperazine (Prazosin);

Class (A4):
the following groups of compounds belong to this class:
(A4a):

β-[(2-methylpropoxy) methyl]-N-phenyl-N-(phenylmethyl)-1-pyrrolidineethanamine (Bepridil), (2S-cis)-3-(acetyloxy)-8-chloro-5-[2-(dimethylamino)ethyl]-2,3-dihydro-2-(4-methoxyphenyl)-1,5-benzothiazepin-4(5H)-one (Clentiazem), (2S-cis)-3-(acetyloxy)-5-[2-(dimethylamino) ethyl]-2,3-dihydro-2-(4-methoxyphenyl)-1,5-benzothiazepin-4 (5H)-one (Diltiazem), γ-phenyl-N-(1-phenylethyl)benzene-propanamine (Fendiline), α[3-[[2-(3,4-dimethoxyphenyl)ethyl]methylamino] propyl]-3,4,5-trimethoxy-α-(1-methylethyl)-benzeneacetonitrile (Gallopamil), (1S-cis) methoxyacetic acid 2-[2[[3-(1H-benzimidazol-2-yl)propyl]methylamino]ethyl]-6-fluoro-1,2,3,4-tetrahydro-1-(1-methylethyl)-2-naphthalenyl ester (Mibefradil), N-(1-methyl-2-phenylethyl)-γ-phenylbenzenepropanamine (Prenylamine), (R)-2-[2-[3-[[2-(1,3-bezodioxol-5-yloxy)ethyl]methylamino]propoxy]-5-methoxyphenyl]-4-methyl-2H-1,4-benzothiazin-3(4H)-one (Semotiadil), N-(1,1-dimethylethyl)-α-methyl-γ-phenylbenzenepropanamine (Terodiline), α-[3-[[2-(3,4-dimethoxyphenyl)ethyl]methylamino]propyl]-3,4-dimethoxy-α-(1-methylethyl)-benzeneacetonitrile (Verapamil);

(A4b):

2-[(2-aminoethoxy)methyl]-4-(2-chlorophenyl)-1,4-dihydro-6-methyl-3,5-pyridynedicarboxylic acid 3-ethyl 5-methyl ester (Amlodipine), 1,4-dihydro-2,6-dimethyl-4-(2-nitrophenyl)-3,5-pyridinedicarboxylic acid methyl 2-oxopropyl ester (Aranidipine), [S-(R.,R.)]-1,4-dihydro-2,6-dimethyl-4-(3-nitrophenyl)-3,5-pyridinedicarboxylic acid methyl 1-(phenylmethyl)-3-pirrolidinyl ester (Barnidipine), (R.,R.)-±-1,4-dihydro-2,6-dimethyl-4-(3-nitrophenyl)-3,5-pyridinedicarboxylic acid methyl 1-(phenylmethyl)-3-piperidinyl ester (Benidipine) (E)-±-1,4-dihydro-2,6-dimethyl-4-(3-nitrophenyl)-3,5-pyridinedicarboxilic acid 2-methoxyethyl 3-phenyl-2-propenyl ester (Cilnidipine), 5-(5,5-dimethyl-1,3,2-dioxaphosphorinane-2-yl)-1,4-dihydro-2,6-dimethyl-4-(3-nitrophenyl)-3-pyridinecarboxylic acid 2-[phenyl(phenylmethyl)amino] ethyl ester P-oxide (Efonidipine), ±-4-(1,3-benzodioxol-4-yl)-1,4-dihydro-2,6-dimethyl-3,5-pyridinedicarboxylic acid 2-[[(4-fluorophenil)methyl]methylamino]ethyl1-methylethylester (Elgodipine), 4-(2,3-dichlorophenyl)-1,4-dihydro-2,6-dimethyl-3,5-pyridinedicarboxilic acid ethyl methyl ester (Felodipine) 4-(4-benzofurazanyl)-1,4-dihydro-2,6-dimethyl-3,5-pyridinedicarboxylic acid 5-methyl 3-(1-methyl)ethyl ester (Isradipine), (E)-4-[2-[3-(1,1-dimethylethoxy)-3-oxo-1-propenyl]phenyl]-1,4-dihydro-2,6-dimethyl-3,5-pyridinedicarboxylic acid diethyl ester (Lacidipine), 1,4-dihydro-2,6-dimethyl-4-(3-nitrophenyl)-3,5-pyridinedi-carboxilic acid 2-[(3,3-diphenyl-propyl)methylamino]-1,1-dimethylethyl methyl ester (Lercanidipine), 1,4-dihydro-2,6-dimethyl-4-(3-nitrophenyl)-3,5-pyridinedicarboxilic acid 2-[4-(diphenylmethyl)-1-piperazinyl]ethyl methyl ester (Manidipine), 1,4-dihydro-2,6-dimethyl-4-(3-nitrophenyl)-3,5-pyridinedicarboxylic acid methyl 2[methyl-(phenylmethyl)amino]ethyl ester (Nicardipine), 1,4-dihydro-2,6-dimethyl-4-(2-nitrophenyl)-3,5-pyridinedicarboxylic acid dimethyl ester (Nifedipine), 2-cyano-1,4-dihydro-6-methyl-4-(3-nitrophenyl)-3,5-pyridinedicarboxylic acid 3-methyl 5-(1-methylethyl) ester (Nilvadipine), 1,4-dihydro-2,6-dimethyl-4-(3-nitrophenyl)-3,5-pyridinedicarboxylic acid 2-methoxyethyl 1-methylethyl ester (Nimodipine), 1,4-dihydro-2,6-dimethyl-4-(2-nitrophenyl)-3,5-pyridinedicarboxylic acid methyl 2-methylpropyl ester (Nisoldipine), 1,4-dihydro-2,6-dimethyl-4-(3-nitrophenyl)-3,5-pyridinedicarboxylic acid ethyl methyl ester (Nitrendipine);

(A4c):

1-(diphenylmethyl)-4-(3-phenyl-2-propenyl)piperazine (Cinnarizine), (E)-1-[bis(4-fluorophenyl)methyl]4-(3-phenyl-2-propenyl) piperazine (Flunarizine) 4-[4,4-bis (4-fluorophenyl)butyl]-N-(2,6-dimethylphenyl)-1-piperazineacetamide (Lidoflazine), 1-[bis(4-fluorophenyl) methyl]-4-[(2,3,4-trimethoxyphenyl)methyl]piperazine (Lomerizine);

(A4d)

N,N-dimethyl-3-[[1-(phenylmethyl)-cycloheptyl]oxy]-1-propanamine (Bencyclane), 1-[2-[2-(diethylamino)ethoxy]phenyl]-3-phenyl-1-propanone (Etafenone), 3,4-dimethoxy-N-methyl-N-[3-[4-[[2-(1-methylethyl)-1-indolizinyl]sulphonyl]phenoxy]-propyl]benzeneethanamine (Fantofarone);

Class (A7):

the following groups of compounds belong to this class:
(A7a):

6-chloro-3,4-dihydro-3-[(2-propenylthio)methyl]-2H-1,2,4-benzothiadiazine-7-sulphonamide 1,1-dioxide (Althiazide), 3,4-dihydro-3-(phenylmethyl)-6-(trifluoromethyl)-2H-1,2,4-benzothiadiazine-7-sulphonamide 1,1-dioxide (Bendroflumethiazide), (6-chloro-3-[[(phenylmethyl)thio]methyl]-2H-1,2,4-benzothiadiazine-7-sulphonamide 1,1-dioxide (Benzthiazide), 6-chloro-3,4-dihydro-3-(phenylmethyl)-2H-1,2,4-benzothiadiazine-7-sulphonamide 1,1-dioxide (Benzylhydrochlorothiazide), 6-chloro-3,4-dihydro-3-(2-methylpropyl)-2H-1,2,4-benzothiadiazine-7-sulphonamide 1,1-dioxide (Buthiazide), 6-chloro-2H-1,2,4-benzothiadiazine-7-sulphonamide 1,1-dioxide (Chlorothiazide), 2-chloro-5-(2,3-dihydro-1-hydroxy-3-oxo-1H-isoindol-1-yl)benzebesulphonamide (Chlorthalidone), 6-chloro-3-(cyclopentylmethyl)-3,4-dihydro-2H-1,2,4-benzothiadiazine-7-sulphonamide 1,1-dioxide (Cyclopenthiazide), 3-bicyclo [2.2.1]-hept-5-en-2-yl-6-chloro-3,4-dihydro-2H-1,2,4-benzothiadiazine-7-sulphonamide 1,1-dioxide (Cyclothiazide), 6-chloro-3,4-dihydro-3-[[(2,2,2-trifluoroethyl)tio]methyl]-2H-1,2,4-benzothiadiazine-7-sulphonamide 1,1-dioxide (Epithiazide), 6-chloro-3-ethyl-3,4-di-hydro-2H-1,2,4-benzothiadiazine-7-sulphonamide 1,1-dioxide (Ethiazide), 7-chloro-1,2,3,4-tetrahydro-4-oxo-2-phenyl-6-quinazolinesulphonamide (Fenquizone), 3-(aminosulphonyl)-4-chloro-N-(2,3-dihydro-2-methyl-1H-indol-1-yl)benzamide (Indapamide), 6-chloro-3,4-dihydro-2H-1,2,4-benzothiadiazine-7-sulphonamide 1,1-dioxide (Hydrochlorothiazide), 3,4-dihydro-6-(trifluoromethyl)-2H-1,2,4-benzothiadiazine-7-sulphonamide 1,1-dioxide (Hydroflumethiazide), 6-chloro-3-(chloromethyl)-3,4-dihydro-2-methyl-2H-1,2,4-benzothiadiazine-7-sulphonamide 1,1-dioxide (Methyclothiazide), 3,4-dihydro-6-methyl-2H-1-benzothiopyran-7-sulphfonamide 1,1-dioxide (Methycrane), 7-chloro-1,2,3,4-tetrahydro-2-methyl-3-(2-methylphenyl)-4-oxo-6-quinazolinesulphonamide (Metolazone), 6-chloro-3-[[(4-fluorophenyl)methyl]-3,4-dihydro-2H-1,2,4-benzothiadiazine-7-sulphonamide 1,1-dioxide (Paraflutizide) 6-chloro-3,4-dihydro-2-methyl-3-[(2,2,2-trifluoroethyl)thio]methyl]-2H-1,2,4-benzothiadiazine-7-sulphonamide 1,1-dioxide (Polythiazide), 7-chloro-2-ethyl-1,2,3,4-tetrahydro-4-oxo-6-quinazolinesulphonamide (Quinethazone), 6-chloro-3,4-dihydro-3-trichloromethyl-2H-1,2,4-benzothadiazine-7-sulphonamide 1,1-dioxide (Teclothiazide), 6-chloro-3-(dichloromethyl)-3,4-dihydro-2H-1,2,4-benzothadiazine-7-sulphfonamide 1,1-dioxide (Trichlormethiazide);

(A7b):

3,7-dihydro-1,3-dimethyl-7-(4-morpholinylmethyl)-1H-purine-2,6-dione (7-Morpholinomethyltheophylline), 3,7-dihydro-1-(2-hydroxypropyl)-3,7-dimethyl-1H-purine-2,6-dione (Protheobromine), 3,7-dihydro-3,7-dimethyl-1H-purine-2,6-dione (Theobromine);

(A7c)

6-amino-3-ethyl-1-(2-propenyl)-2,4 (1H, 3H)-pyrimidinedione (Aminometradine), 6-amino-3-methyl-1-(2-methyl-2-propenyl)-2,4(1H,3H)-pyrimidinedione (Amisometradine);

(A7d):

N-phenyl-1,3,5-triazine-2,4-diamine (Amanozine), 3,5-diamino-N-(aminoiminomethyl)-6-chloropyrazinecarboxamide (Amiloride), N-(4-chlorophenyl)-1,3,5-triazine-2,4-diamine (Chlorazanyl), [3-methyl-4-oxo-5-(1-piperidinyl)-2-thiazolidinylidene] acetic acid ethyl ester (Etozolin), 6-hydrazino-3-piridazinecarboxamide (Hydracarbazine), 5-amino-2[1-(3, 4-dichlorophenyl)ethyl]-2,4-dihydro-3H-pyrazol-3-one (Muzolimine), 2-(2,2-dicylcohexylethyl)piperidine (Perhexiline), 6-phenyl-2,4,7-pteridinetriamine (Triamterene), 3-(aminosulphonyl)-5-(butylamino)-4-phenoxybenzoic acid (Bumetanide), 5-(amino sulphfonyl)-4-chloro-2-[(2-furanylmethyl)amino]benzoic acid (Furosemide), N-[[1-methylethyl)amino]carbonyl]-4-[(3-methylphenyl)amino]-3-3-pyridinesulphonamide (Torasemide);

Class (A8): Apomorphine.

The preferred compounds in the (A1b) class are the following: when $X_{A1}$=(IXa), $R_{A1}$=$CH_2OH$, $R^I_{A1}$=Cl, $R^{III}_{A1}$=$R^{IV}_{A1}$=free valences forming a —CH=CH— double bond with the carbon atoms in 4 and 5 position of the heterocyclic ring of the formula (A1b), $R^{II}_{A1}$=—$(CH_2)_3$—$CH_3$, Losartan residue;

as in Losartan but with $R_{A1}$=—O and $R^{III}_{A1}$ free valence, so as to form in combination with the carbon atom in 5 position of the heterocyclic ring of the formula (A1b) a ketonic group, $R^I_{A1}$ with $R^{IV}_{A1}$ and with the carbon atom in 4 position of the heterocyclic ring are such as to form the saturated ring having 5 carbon atoms (IXd), Irbesartan residue;

as in Losartan but with $R^{IV}_{A1}$=—O—$CH_2$—$CH_3$, $R_{A1}$ together with $R^I_{A1}$ and the carbon atoms in 4 and 5 position of the heterocyclic ring with $R^{IV}_{A1}$ and $R^{III}_{A1}$ free valences, are such as to form the aromatic radical containing a —COOH group (IXc), Candesartan residue;

as in Losartan but with $X_{A1}$=—COOH, $R_{A1}$=(IXb), $R^I_{A1}$=H, $R^{IV}_{A1}$ and $R^{III}_{A1}$ free valences form a double bond between the carbon atoms in 4 and 5 position in the heterocyclic ring of the formula (A1b), Eprosartan residue.

The preferred compounds of the A2 class are the following:

1-[[3-(4,7-dihydro-1-methyl-7-oxo-3-propyl-1H-pyrazol[4,3-d]-pyrimidin-5-yl)-4-ethoxyphenyl]sulfonyl]-4-methyl-piperazine (Sildenafil), 2-(2-propyloxyphenyl)-8-azapurin-6-one (Zaprinast).

The preferred compounds of the A3 class are the following:

when $R^I_{B1}$=H, $R^{II}_{B1}$ and $R^{III}_{B1}$=$CH_3$, $R^V_{B1}$=H, $R^{VI}_{B1}$=$R^{VII}_{B1}$=H, m=n=1, $X_{B1}$=—O—, $R^{IV}_{B1}$=(XIp) wherein $S_1$=$S_2$=$S_4$=H, $S_3$=—$CH_2$—CO—$NH_2$, Atenolol residue;

as in Atenolol but with $R^{IV}_{B1}$=(XIs), Befunolol residue;
as in Atenolol, but with $S_3$=$S_2$=$S_4$=H, $S_1$=—$CH_2$—CH=$CH_2$, Alprenolol residue;
as in Atenolol, but with $S_1$=$COCH_3$, $S_3$=—NH—CO—$(CH_2)_2$—$CH_3$, $S_2$=$S_4$=H, Acebutolol residue;
as in Atenolol, but with $S_3$=—$CH_2$—$CH_2$—O—$CH_2$—(cyclopropyl), Betaxolol residue;
as in Atenolol but with $S_3$=—$CH_2$—O—$CH_2$—$CH_2$—O—$CH(CH_3)_2$, Bisoprolol residue;
as in Alprenolol but with $S_1$=(XIp$^{II}$) and $R^I_{B1}$=$CH_3$, Bufetolol residue;
as in Bufetolol, but with $S_1$=—CN, Bunitrolol residue;
as in Bufetolol, but with $S_1$=H, $S_4$=Cl $S_2$=$CH_3$, Bupranolol residue;
as in Bufetolol but with $S_1$=—CO—$(CH_2)_2$—$CH_3$, $S_3$=F, Butofilolol residue;
as in Atenolol but with $R^{IV}_{B1}$=(XIp$^{VIII}$), wherein B=—NH—, Carazolol residue;
as in Bufetolol, but with $R^{IV}_{B1}$=(XIp$^{VII}$) wherein A=—$CH_2$—$CH_2$—, B=—NH—, W2=—O which with W1=free valence and the carbon atom in 1' position forms a ketonic group, Carteolol residue;
as in Bufetolol but with $S_3$=—NH—CO—$N(C_2H_5)_2$, $S_1$=—CO—$CH_3$ Celiprolol residue;
as in Bufetolol but with $S_1$=—O—$CH_2$—CONH—$CH_3$, Cetamolol residue;
as in Bupranolol, but with $S_2$=Cl Cloranolol residue;
as in Atenolol but with $S_3$=—$CH_2$—$CH_2$—$COOCH_3$, Esmolol residue;
as in Atenolol but with $R^{IV}_{B1}$=(Xiu) Indenolol residue;
as in Carteolol, but in $R^{IV}_{B1}$=(XIp$^{VII}$) A=—$CH_2$—, B=—$COCH_2$—, W1=W2=H, Levobunolol residue;
as in Carteolol but with $R^I_{B1}$=H and in $R^{IV}_{B1}$=(XIp$^{VII}$) A is a tertiary carbon atom and W1 free valence, so as to form a —CH=CH— double bond between A and the carbon atom in 1' position of (XIp$^{VII}$), W2=$CH_3$, Mepindolol residue;
as in Atenolol, but with $S_3$=—$(CH_2)_2$—$OCH_3$, Metoprolol residue;
as in Carteolol but in $R^{IV}_{B1}$=(XIp$^{VII}$) A=—$CH_2$—CH(OH)—, B=—$CH_2$—, W2=OH, W1=H. Nadolol residue;
as in Atenolol but with $S_3$=$NO_2$, Nifenalol residue;
as in Mepindolol but in $R^{IV}_{B1}$=(XIp$^{VII}$) A=—O—$CH_2$—, B=—$CH_2$—, W2=—$ONO_2$, W1=H, Nipradilol residue;
as in Alprenolol, but with $S_1$=—O—$CH_2$—CH=$CH_2$, Oxprenolol residue;
as in Bufetolol, but with $S_1$=cyclopentyl, Penbutolol residue;
as in Mepindolol but with W2=H, Pindolol residue;
as in Atenolol but with $S_3$=—NH—$COCH_3$, Practolol residue;
as in Bufetolol but with $S_1$=H, $S_3$=—NH—CO—NH—(cyclohexyl), Talinolol residue;
as in Nipradilol but with $R^I_{B1}$=$CH_3$, A=—S—$CH_2$— and W2=H, Tertatolol residue;
as in Tertatolol but with $R^{IV}_{B1}$=(XIn), Tilisolol residue;
as in Bufetolol but with $R^{IV}_{B1}$=(XIo), Timolol residue;
as in Bufetolol but with $S_1$=$S_2$=$CH_3$, Xibenolol residue;
as in Xibenolol but with $R^I_{B1}$=$S_1$=H, Toliprolol residue;
as in Toliprolol, but with $R^{II}_{B1}$=H and $R^{III}_{B1}$=(XIa), Bevantolol residue;
as in Carazolol but with $R^{II}_{B1}$=H and $R^{III}_{B1}$=(XIb), Carvedilol residue;
when in the (A3) formula $R^I_{B1}$=$R^{II}_{B1}$=$R^{III}_{B1}$=$CH_3$, $R^V_{B1}$=(XIh), n=m=1, $R^{VI}_{B1}$=$R^{VII}_{B1}$=H, $X_{B1}$=—O—, $R^{IV}_{B1}$=(XIg), Bopindolol residue;
as in Bufetolol but with $R^{IV}_{B1}$=(XIt), Bucumolol residue;
when in the (A3) formula m=n=0 and $R^{IV}_{B1}$=(XIz) $R^I_{B1}$=$R^{II}_{B1}$=$R^{III}_{B1}$=$CH_3$, $R^V_{B1}$=H, Bufuralol residue;
as in Atenolol but with $R^{III}_{B1}$=(XIe) with $Y_{B1}$=H, n=m=0, $R^{IV}_{B1}$=(XIi) Butidrine residue;

as in Butidrine, but with $RIII_{B1}$=(XIe) with $Y_{B1}$=(XIf) with Z=H, $R^{IV}_{B1}$=(XIp) wherein $S_3$=OH and $S_2$=CONH$_2$, $S_1$=$S_4$=H, Dilevalol residue;

as in Bevantolol but with $S_2$=H, $S_1$=CN, $R^{III}_{B1}$=(XIc), Epanolol residue;

as in Butidrine but with $R^{III}_{B1}$=CH$_3$, $R^{IV}_{B1}$=(XIm), wherein the naphthalenic residue is linked by the carbon atom in 2 position to the carbon atom bringing the —OR$^{IV}_{B1}$ substituent, Pronethalol residue;

as in Pronethalol but with m=1 and $X_{B1}$=—O—, and $R^{IV}_{B1}$ is the naphthalenic residue (XIm) linked by the carbon atom in 1 position to $X_{B1}$ Propranolol residue;

as in Pronethalol but with $R^{IV}_{B1}$=(XIp) with $S_1$=$S_2$=$S_4$=H and $S_3$=—NH—SO$_2$—CH$_3$, Sotalol residue;

as in Dilevalol but with $S_2$=—SOCH$_3$, and in para position to the other aromatic ring (form. XIf) z=—OCH$_3$, Sulfinalol residue;

when in the (A3) formula $R^I_{B1}$=$R^{II}_{B1}$=H, $R^{III}_{B1}$=(XId) with t =1, $R^V_{B1}$=H, n=m=0, $R^{IV}_{B1}$=(XId) with t=0, Nebivolol residue;

2-hydroxy-5-[1-hydroxy-2-[(1-methyl-3-phenylpropyl)amino]ethyl]benzamide (Labetalol), 1-(4-amino-6,7-dimethoxy-2-quinazolinyl)-4-[(tetrahydro-2-furanyl)carbonyl] piperazine (Terazosin), 1-(4-amino-6,7-dimethoxy-2-quinazolinyl)-4-(2-furanylcarbonyl) piperazine (Prazosin), benzonitrile,2-[2-hydroxy-3-([2-(1H-indol-3-yl)-1,1-dimethylethyl]amino]propoxy (Bucindolol).

In the (A4) class the preferred compounds are the following:

(A4a)

(2S-cis)-3-(acetyloxy)-5-[2-(dimethylamino)ethyl]-2,3-dihydro-2-(4-methoxyphenyl)-1,5-benzothiazepin-4 (5H)-one (Diltiazem), α-[3-[[2-(3,4-dimethoxyphenyl)ethyl]methyl amino]propyl]-3,4-dimethoxy-α-(1-methylethyl)benzeneacetonitrile (Verapamil);

(A4b):

2-[(2-aminoethoxy)methyl]-4-(2-chlorophenyl)-1,4-dihydro-6-methyl-3,5-pyridinedicarboxylic acid 3-ethyl 5-methyl ester (Amlodipine), 4-(2,3-dichlorophenyl)-1,4-dihydro-2,6-dimethyl-3,5-pyridinedicarboxylic acid ethyl methyl ester (Felodipine) 4-(4-benzofurazanyl)-1,4-dihydro-2,6-dimethyl-3,5-pyridinedicarboxylic acid 5-methyl 3-(1-methyl)ethyl ester (Isradipine) Lercanidipine, 1,4-dihydro-2,6-dimethyl-4-(3-nitrophenyl)-3,5-pyridinedicarboxylic acid methyl 2[methyl (phenylmethyl)amino]ethyl ester (Nicardipine), 1,4-dihydro-2,6-dimethyl-4-(2-nitrophenyl)-3,5-pyridinedicarboxylic acid dimethyl (Nifedipine), 1,4-dihydro-2,6-dimethyl-4-(3-nitrophenyl) -3,5-pyridinedicarboxylic acid 2-methoxyethyl 1-methylethyl ester (Nimodipine), 1,4-dihydro-2,6-dimethyl-4-(2-nitrophenyl)-3,5-pyridinedicarboxylic acid methyl 2-methyl-propyl ester (Nisoldipine), 1,4-dihydro-2, 6-dimethyl-4-(3-nitrophenyl) -3,5-pyridinedicarboxylic acid ethyl methyl ester (Nitrendipine);

(A4c)

(E)-1-(bis(4-florophenyl)methyl]4-(3-phenyl-2-propenyl) piperazine (Flunarizine).

In class (A7) the preferred compounds are the following:

(A7a):

6-chloro-2H-1,2,4-benzothiadiazine-7-sulphonamide 1,1-dioxide (Chlorothiazide), 2-chloro-5-(2,3-dihydro-1-hydroxy-3-oxo-1H-isoindol-1-yl)benzebesulphonamide (Chlorthalidone), 6-chloro-3,4-dihydro-2H-1,2,4-benzothiadiazine-7-sulphonamide 1,1-dioxide (Hydrochlorothiazide), 3-(aminosulfonyl)-4-chloro-N-(2,3-dihydro-2-methyl-1H-indol-1-yl)benzamide (Indapamide), 7-chloro-1,2,3,4-tetrahydro-2-methyl-3-(2-methylphenyl)-4-oxo-6-quinazolinesulphonamide (Metolazone), 7-chloro-2-ethyl-1,2,3,4-tetrahydro-4-oxo-6-quinazolinesulphonamide (Quinethazone);

(A7d):

3,5-diamino-N-(aminoiminomethyl)-6-chloropyrazinecarboxamide (Amiloride), 6-phenyl-2,4,7-pteridinetriamine (Triamterene), 3-(aminosulphonyl)-5-(butylamino)-4-phenoxybenzoic acid (Bumetanide), 5-(amino sulphonyl)-4-chloro-2-[(2-furanylmethyl)amino] benzoic acid (Furosemide), N-[[(1-methylethyl)amino] carbonyl]-4-[(3-methylphenyl)amino]3-pyridinesulphonamide (Torasemide).

Particularly preferred compounds according to the present invention are the following:

| | |
|---|---|
| Class A1b): | Losartan; |
| Class A2): | Sildenafil, Zaprinast; |
| Class A3): | Atenolol, Labetalol, Timolol, Prazosin, Terazosin, Propanolol; |
| Class A4): | Nicardipine, Nifedipine, Nimodipine; |
| Class A7): | Chlorothiazide, Amiloride, Furosemide. |

The precursors of the salts belonging to the above mentioned classes are prepared according to the methods described in "The Merck Index 12$^a$ Ed." (1996), herein incorporated by reference. The Zaprinast preparation method is described in the DE patent 2,162,096. The Bucindolol preparation method is described in the G.B. patent 2,001,633.

In the compositions according to the present invention also the isomers of the compounds belonging to the above described classes can be used. Example of isomers are cis-, trans-, optical isomer D and L or the racemic, enantiomer. In general one isomeric form has higher activity with respect to the other, e.g., D form with respect to L form or vice versa.

The salts of the compounds belonging to these classes contain at least a nitrate ion mole/compound mole. Preferably the ratio between the nitrate ion moles and the precursor ones is unitary. Salts having higher molar ratio are obtained when in the molecule other aminic groups basic enough to be salified are present.

The salts of the present invention are formulated in the corresponding pharmaceutical compositions according to the well known techniques in the field, together with the usual excipients; see for example the "Remington's Pharmaceutical Sciences 15a Ed." volume.

The dose of the invention salts in their pharmaceutical compositions are the same, and generally lower than those of their precursors of the mentioned classes.

The salts of the present invention are obtainable according to one of the following methods:

When the substance to be salified is available as free base or as a corresponding salt soluble in an organic solvent, which preferably does not contain hydroxyl groups, for example acetonitrile, ethyl acetate, tetrahydrofuran, etc., the salt is prepared by dissolving the substance in the solvent at a concentration preferably equal to or higher than 10% w/v, adding the amount of concentrated nitric acid corresponding to the moles of salifiable aminic groups present in the compound. The nitric acid is preferably diluted in the same solvent. Preferably during and after the addition the mixture is cooled to temperatures in the range 20° C.–0° C. The product is generally recovered by filtration and washed with the solvent.

When on the contrary the substance is not very soluble, or it is available as a not very soluble salt in the above mentioned solvents, the corresponding mixtures with hydroxylated solvents can be used. Examples of such solvents are methyl alcohol, ethyl alcohol and water. Precipitation can be quickened by diluting then the so obtained mixture, after the addition of nitric acid, with an apolar solvent.

When the starting product is salified with hydrochloric acid, it is possible to prepare the salt with nitric acid directly adding silver nitrate to the compound solution. After filtering silver chloride, the solution is concentrated and cooled to recover the nitrate salt.

When the starting product is a salt, it is also possible to liberate the corresponding base by a treatment with a sodium or potassium bicarbonate or carbonate saturated solution, or with a sodium or potassium hydroxide diluted solution. The base is then extracted by a suitable organic solvent (for example halogenated solvents, esters, ethers), which is then dried. The organic solution is evaporated and then one proceeds according to the preceding preparation methods, by dissolving the base in acetonitrile or in the other above mentioned solvents.

The nitrate salts can be obtained also by using precursors of the described classes containing in the molecule a —$ONO_2$ group bound by a linking bridge prepared as described in the European patent 759,899 in the name of the Applicant herein incorporated by reference.

The following examples are given only for illustrative purposes and they are not a limitation of the same.

EXAMPLE 1

Timolol Nitrate Salt Preparation

To a saturated aqueous solution of sodium bicarbonate (100 ml) the timolol maleate salt (7 g) is added. The mixture is extracted with ethyl acetate (300 ml). The organic phase is dried by sodium sulphate and then evaporated under vacuum, obtaining the corresponding Timolol base (4.9 g) which is dissolved in acetonitrile (25 ml). The solution cooled with ice is treated with a 65% nitric acid solution (1.08 ml) in acetonitrile (5 ml) and after 30 minutes under stirring at cold it is treated with ethyl ether (100 ml) to give a solid which is filtered, washed with ethyl ether and dried under vacuum. 4.6 g of Timolol nitrate salt m.p. 115°–1160° C., are obtained.

$^1$H-NMR ($D_2O$) ppm: 4.34 (1H, m), 3.76 (4H, t), 3.39 (4H, t), 3.23 (2H, m), 3.04 (2H, m) 1.29 (9H, s).

Elementary analysis ($C_{13}H_{25}N_5O_6S$):

| calc. (%) | C 41.15 | H 6.64 | N 18.46 | S 8.45 |
|---|---|---|---|---|
| found (%) | C 41.24 | H 6.61 | N 18.38 | S 8.31 |

EXAMPLE 2

Propranolol Nitrate Salt Preparation

To a saturated aqueous solution of sodium bicarbonate (70 ml) the propranolol hydrochloride salt (5 g) is added. The mixture is extracted with ethyl acetate (250 ml). The organic phase is dried by sodium sulphate and then evaporated under vacuum, obtaining the corresponding Propranolol base (4.2 g) which is dissolved in acetonitrile/tetrahydrofuran 5/2 (70 ml). The solution cooled with ice is treated with a 65% nitric acid solution (1.13 ml) in acetonitrile (10 ml) and after 30 minutes under stirring at cold it is treated with ethyl ether (50 ml) to give a solid which is filtered, washed with ethyl ether and dried under vacuum. 5.1 g of Propranolol nitrate salt m.p. 127°–130° C. are obtained.

$^1$H-NMR ($D_2O$) ppm: 8.15 (1H, m), 7.80 (1H, m), 7.48–7.32 (4H, m), 6.86 (1H, d), 4.32 (1H, m) 4.13 (2H, d) 3.36 (1H, m), 3.22 (2H, d), 1.24 (6H, d).

Elementary analysis ($C_{16}H_{22}N_2O_5$):

| calc. (%) | C 59.62 | H 6.88 | N 8.69 |
|---|---|---|---|
| found (%) | C 59.99 | H 6.97 | N 8.65 |

EXAMPLE 3

Sildenafil Nitrate Salt Preparation

A Sildenafil solution (7.7 g, 16.3 mmoles) in a mixture of acetonitrile (100 ml) and tetrahydrofuran (40 ml) is treated with 65% nitric acid (1.13 ml) dissolved in acetonitrile (10 ml). After 30 minutes at +4° C., it is concentrated to small volume by evaporation at reduced pressure and ethyl ether (100 ml) is slowly added. The formed precipitate is filtered, washed with ethyl ether and dried under vacuum. A white amorphous solid (6.5 g) is obtained.

Elementary analysis ($C_{22}H_{31}N_7O_7S$):

| calc. (%) | C 49.15 | H 5.81 | N 18.24 | S 5.96 |
|---|---|---|---|---|
| found (%) | C 49.34 | H 5.75 | N 18.38 | S 6.00 |

EXAMPLE 4

Valsartan Nitrate Salt Preparation

A Valsartan solution (3.48 g, 8 mmoles) is prepared by dissolving in a mixture of acetonitrile (30 ml) and tetrahydrofuran (10 ml). Nitric acid diluted in acetonitrile is added at cold (2 ml taken from a solution obtained by adding to 2.7 ml of 65% nitric acid in acetonitrile and bringing to the final volume of 10 ml). After 30 minutes ethyl ether (100 ml) is slowly added at the same temperature (+4° C.). A precipitate is formed which is filtered, washed with ethyl ether and dried under vacuum. A white amorphous solid (3.1 g) is obtained.

Elementary analysis ($C_{24}H_{30}N_6O_6$):

| calc. (%) | C 57.82 | H 6.07 | N 16.86 |
|---|---|---|---|
| found (%) | C 58.02 | H 6.02 | N 16.77 |

EXAMPLE 5

Hydralazine Nitrate Salt Preparation

Hydralazine hydrochloride (3 g) is added to a potassium carbonate aqueous solution (50 ml). It is extracted with ethyl acetate (80 ml). The organic phase is washed with water, dried by sodium sulphate and evaporated under vacuum. The residue (1 g, 6.25 mmoles) is dissolved in a mixture of acetonitrile (30 ml) and methanol (20 ml). It is cooled at +4° C. and a 65% nitric acid solution (0.6 g, 6.24 mmoles) in acetonitrile (10 ml) is added. A white precipitate is formed, which is filtered and dried under vacuum (1 g, m.p. 237°–243° C.).

Elementary analysis ($C_8H_9N_5O_3$):

| calc. (%) | C 43.05 | H 4.06 | N 31.38 |
|---|---|---|---|
| found (%) | C 43.32 | H 4.03 | N 31.22 |

EXAMPLE 6

Nicardipine Nitrate Salt Preparation

A Nicardipine hydrochloride solution (0.1 g, 0.194 mmoles) in acetonitrile (20 ml) is treated in the dark with silver nitrate (0.33 g, 0.194 mmoles). By keeping under stirring at room temperature for 30 minutes, the precipitate is formed as a white solid. It is filtered, concentrated to half volume at a reduced pressure, cooled to +4° C. and it is treated with ethyl alcohol. The precipitate is filtered. It is dried. A yellow solid is obtained (0.05 g, m.p. 193°–198° C.).

Elementary analysis ($C_{26}H_{30}N_4O_9$):

| calc. (%) | C 57.56 | H 5.57 | N 10.33 |
|---|---|---|---|
| found (%) | C 57.44 | H 5.63 | N 10.44 |

EXAMPLE 7

Verapamil Nitrate Salt Preparation

A Verapamil hydrochloride solution (3.44 g, 7 mmoles) in a mixture of acetonitrile (50 ml) and tetrahydrofuran (15 ml) is treated in the dark with silver nitrate (1.19 g, 7 mmoles) The solution is kept under stirring at room temperature for one hour. The precipitate is slowly formed and is filtered at the end. The solution is concentrated to half volume, cooled to +4° C. and the formed precipitate is filtered. After drying, a white amorphous solid is obtained (2.8 g).

Elementary analysis ($C_{27}H_{39}N_3O_7$):

| calc. (%) | C 62.65 | H 7.59 | N 8.12 |
|---|---|---|---|
| found (%) | C 62.48 | H 7.68 | N 8.11 |

EXAMPLE 8

Amiloride Nitrate Salt Preparation

An amiloride hydrochloride solution (2 g, 7.5 mmoles) in methanol (100 ml) is treated with silver nitrate in the dark (1.28 g, 7.5 mmoles). A precipitate is quickly formed. It is left under stirring for 30 minutes at room temperature. Finally the solid is filtered and the solution is concentrated at reduced pressure to half of the initial volume. It is treated with ethyl ether (50 ml) and, after cooling at +4° C., the obtained solid is filtered. After drying a solid is separated (0.8 g, m.p. >280° C.)

Elementary analysis ($C_6H_9ClN_8O_4$):

| calc. (%) | C 24.63 | H 3.10 | N 38.29 | Cl 12.11 |
|---|---|---|---|---|
| found (%) | C 24.75 | H 3.03 | N 38.19 | Cl 12.24 |

EXAMPLE 9

Study of the Effects of Propranolol, Propranolol Nitrate, Timolol and Timolol Nitrate on the Experimental Bronchoconstriction in the Guinea Pig The compounds at a dose of 10 mg/kg and the corresponding carrier have been administered to the guinea pigs (groups of 6 animals each) by intraperitoneal route for three consecutive days.

The animals were prepared according to the method of Del Soldato et al. J. Pharmacol. Methods 5 279 1981. 45 minutes later 0.1 ml of a Capsaicin saline solution (1 $\mu$g/Kg) was injected to the animals intravenously. The tidal air variation before and after the Capsaicin administration was measured by a Konzett apparatus, modified as described in the above mentioned reference, connected to a polygraphic system.

The effects of the compounds and of their corresponding nitrate salts on the experimental bronchoconstriction induced in guinea pigs by the Capsaicin injection are reported in Table 1.

TABLE I

| Treatment | Bronchoconstrictive effect (%) |
|---|---|
| Carrier | 100 |
| Timolol | 188 |
| Timolol.$HNO_3$ | 94 |
| Propranolol | 280 |
| Propranolol.$HNO_3$ | 110 |

EXAMPLE 10

Pharmacological Activity of Sildenafil Nitrate in Comparison with Sildenafil

The compounds have been administered in physiological solution. The control group has been treated with the carrier (physiologic solution) only.

The vaso-relaxing activity of Sildenafil nitrate was determined by using the experimental model of the prostatic deferent vessels constriction, induced by submaximum electric stimulation (D. A. Taylor et al., J. Pharmacol. Exp. Ther. 224, 40–45 1983), in rats treated with $N^w$-nitro-L-arginine methyl ester (L-NAME) as described by Ribeiro et al., Hypertension, 20, 298, 1992. Wistar adult male rats (235–284 g) for a period of 6 weeks received in drinking water L-NAME at a 60–70 mg/100 ml concentration, equivalent to a daily dose of about 60 mg/Kg. The animals received for five days by subcutaneous route a daily dose of 10 mg/kg of Sildenafil nitrate, of Sildenafil or of the carrier, respectively. One hour after the last treatment,. the animals were sacrificed and the prostatic part of the deferent vessel was removed, dipped in a physiologic solution at 37° C., and contracted by transmural stimulation (95% of the maximum stimulation, 0.2 Hz).

The reduction of the neurogenic contractive response, which results within 5 minutes from the addition of the tested substance at a concentration of $10^{-6}$ M, is taken as a measure of the vasorelaxing activity.

TABLE II

| Treatment | Effect on vasoconstriction (%) |
| --- | --- |
| Carrier | 100 |
| Sildenafil.HNO$_3$ | 25 |
| Sildenafil | 68 |

As it is evident from the Table, the myorelaxing activity of the nitrate salt is greater than that of the precursor reference compound.

The relaxation effect of the cavernous artery and of the human cavernosum corpora (vasodilating effect at a peripheric level) was also studied. It was used the technique described by R. G. Hempelmann et al., European Journal of Pharmacology 276, 277–280 (1995), employing erectile tissues coming from patients submitted to surgical operation. The cavernous arteries have been isolated and cleaned up from the surrounding connective tissue. Segments of about 2 mm length were obtained and were mounted in a myograph equipment.

After having drawn an experimental curve diameter/tension, the specimens have been adjusted to a diameter corresponding to 90% of the one reached in the presence of a transluminal pressure of 100 mm Hg; after a stabilization period of about 60 minutes, contraction was effected by adrenaline $3.10^{-6}$ M. After 15 minutes a dose corresponding to $10^{-6}$ M of each of the tested compounds was added and the relaxation percentage was recorded. The results are reported in Table III.

A second series of experiments has been carried out according to the same protocol, on the isolated strips, 3×3×5 mm, of cavernous tissue, isometrically suspended in baths for isolated organs, under a 5–10 mN tension. The results are reported in Table IV.

TABLE III

| Treatment | Relaxing effect on the isolated human cavernous artery pre-contracted with adrenaline (n = 5) (relaxation %) |
| --- | --- |
| Sildenafil $10^{-6}$ M | 25 ± 4 |
| SIN-1 $10^{-6}$ M | 36 ± 7 |
| Sildenafil.HNO$_3$ $10^{-6}$ M | 61 ± 3 |

TABLE IV

| Treatment | Relaxing effect on the isolated human cavernous tissue precontracted with adrenaline (n = 4) (relaxation %) |
| --- | --- |
| Sildenafil $10^{-6}$ M | 42 ± 6 |
| SIN-1 $10^{-6}$ M | 33 ± 4 |
| Sildenafil.HNO$_3$ $10^{-6}$ M | 68 ± 7 |

In both the above experimental models it was evident a relaxation effect of the contraction induced by adrenaline both following to Sildenafil treatment, and to that with the nitric oxide SIN-1 donor. The derivative according to the present invention has shown an higher pharmacological effect than the precursor Sildenafil and SIN-1.

EXAMPLE 11

Study of the Antihypertensive and Anti-angiotensinic Activity of Losartan Nitrate Compared with Losartan The compounds have been administered in physiologic solution. The control group has been treated with the carrier (physiological solution) only.

The inhibiting effect of Losartan nitrate on the arterial hypertension has been assayed by using two experimental models: the arterial hypertension induced by L-NAME (see the preceding example) and the muscular contraction produced by Angiotensin II. In the first experiment Wistar adult male rats (235–284 g) received for 6 weeks drinking water containing L-NAME. at a 60–70 mg/100 ml concentration, equivalent to a daily dose of about 60 mg/Kg. The animals received for five days subcutaneously a daily dose of 10 mg/kg of Losartan nitrate, Losartan or the carrier, respectively. One hour after the last treatment, the systemic arterial pressure was determined by caudal way, as described by Zatz, Lab. Anim. Sci., 42, 198, 1990.

In the second experiment (contraction produced by Angiotensin II), the method described by P. C. Wong et al., Hypertension, 13, 489–497, 1989 has been followed. Segments of the isolated ileum taken from guinea pigs (300–350 g) were dipped in a physiologic solution containing Angiotensin II (10 mcg/ml), Angiotensin II+Losartan nitrate $10^{-6}$M, and Angiotensin II+Losartan $10^{-6}$M, respectively. The results are reported in Table V.

TABLE V

| Treatment | Average arterial pressure (mm Hg) | Effect on the contraction of the smooth musculature % (n = 5) |
| --- | --- | --- |
| Carrier | 170 ± 7 | 100 |
| Losartan.HNO$_3$ | 115 ± 4 | 12 |
| Losartan | 153 ± 5 | 33 |

From the Table it is seen that the inhibiting effect of the nitrate salt on the hypertension produced by by L-NAME is greater than that of the precursor reference compound. The two products are both effective on myorelaxing activity since they inhibit the contraction induced by Angiotensin II, but the compound according to the invention shows an higher efficacy.

EXAMPLE 12

Study of the Antihypertensive and Vaso-relaxing Activity of Minoxidil Nitrate Compared with Minoxidil The compounds have been administered in a physiologic solution. The control group was treated with the carrier (physiologic solution) only.

The inhibiting effect of Minoxidil nitrate on the arterial hypertension has been determined by using two experimental models: the arterial hypertension induced by L-NAME (see Example 10) and the vascular contraction induced by electric stimulation. In the first pharmacological experiment the rats have been treated as described in the pharmacological experiment with L-NAME of Example 11. In the second experiment the method described by Taylor (see Example 10) has been followed as described before. The prostatic part of the isolated deferent duct of rats (200–220 g) was removed and dipped in a physiologic solution at 37° C. and then contracted by transmural stimulation (95% of the maximum stimulation, 0.2 Hz).

The vasorelaxing activity is expressed as the reduction of the contractive neurogenic response, determined within 5 minutes from the. addition of the tested compound at a $10^{-6}$ M concentration.

TABLE VI

| Treatment | Average arterial pressure (mm Hg) | Effect on the vasoconstriction % (n = 5) |
| --- | --- | --- |
| Carrier | 170 ± 7 | 100 |
| Minoxidil.HNO$_3$ | 110 ± 6 | 5 |
| Minoxidil | 132 ± 6 | 18 |

As it is evident from Table VI, the inhibiting effect of Minoxidil nitrate salt on the hypertension produced by L-NAME in greater than that of the reference compound. As regards the vaso-relaxing activity, the two products are both effective in the inhibiting the vasoconstriction induced by the electric stimulation.

EXAMPLE 13

Study of the Antihypertensive and Beta-adrenolytic Activity of Timolol Nitrate Compared with Timolol Two experimental models were used: the arterial hypertension produced by L-NAME and the inatropic-positive effect caused by Isoprenaline.

In the former experiment the antihypertensive activity has been studied according to the experimental model described in Example 11.

In the latter experiment the method described by Grodzinski et al., Arch. Int. Phramacodyn., 191, 133–141, 1971 was followed. The left atrium specimens taken from guinea pigs (300–350 g) were maintained at 32° C. in a physiologic solution wherein the concentration of calcium ion was ⅓ lower and stimulated by Isoprenaline (10 mcg/ml). The beta-adrenolitic activity is expressed as the reduction of the inotropic-positive effect (increase of the cardiac muscle contraction) following addition of the compound under examination at a $10^{-6}$M concentration.

TABLE VII

| Treatment | Average arterial pressure (mm Hg) | Inotropic positive effect % (n = 5) |
| --- | --- | --- |
| Carrier | 170 ± 7 | 100 |
| Timolol.HNO$_3$ | 108 ± 8 | 13 |
| Timolol | 144 ± 5 | 32 |

As it is evident from Table VII, the inhibition effect of. the Timolol nitrate salt on the hypertension produced by L-NAME is greater than that of Timolol. As regards the adrenolytic activity, the two products are both effective in inhibiting the inotropic-positive effect caused by Isoprenaline, but that according to the invention shows an higher efficacy.

EXAMPLE 14

Study of the Antihypetensive and Calcium Antagonist Activity of Nicardipine Nitrate Salt Compared with Nicardipine Two experimental models were used: the arterial hypertension induced by L-NAME and the muscular contraction induced by calcium chloride.

In the former experiment the antihypertensive activity was studied according to the experimental model described in Example 11.

In the latter, the experimental model adapted was that of the ileal contraction caused by calcium chloride, according to the method described by M. J. Spedding, J. Pharmacology 83, 211–220, 1984. Ileus segments taken from guinea pig (300–350 g) were maintained at 37° C. in a physiologic solution not containing calcium ions and then stimulated by calcium chloride addition (final concentration 20 mcg/ml). The calcium antagonist activity was determined as the reduction of the ileal contraction following addition of each of the test compounds at a concentration $10^{-6}$ M.

TABLE VIII

| Treatment | Average arterial pressure (mm Hg) | Contracturing effect % (n = 5) |
| --- | --- | --- |
| Carrier | 170 ± 7 | 100 |
| Nicardipine.HNO$_3$ | 108 ± 3 | 8 |
| Nicardipine | 122 ± 6 | 25 |

As it is evident from the Table, the inhibiting effect of the nitrate salt on the hypertension induced by L-NAME is greater than that of the precursor Nicardipine. As regards the calcium antagonist activity the two compounds appeared both effective in inhibiting the contracturing calcium-depending effect, even if in a different extent.

EXAMPLE 15

Study of the Antihypertensive and Diuretic Activity in Rats of the Amiloride Nitrate Salt Compared with Amiloride The Amiloride pharmacological profile has been determined by using the following experimental models: the arterial hypertension produced by L-NAME, and the diuretic effect.

In the former experiment the antihypertensive activity has been studied according to the experimental model described in Example 11.

In the latter experiment the diuretic effect was studied according to the method described by W. L. Lipschwitz et al. J. Pharmacol. Exp. Ther., 79, 97–110, 1943. No 3 groups of 6 rats (200–220 g) each, stalled in metabolic cages received drinking distilled water (25 ml/Kg p.o.). Each group was then subcutaneously injected with Amiloride nitrate (10 mg/Kg), Amiloride (10 mg/Kg) or carrier respectively. The urine volume was collected during a period of 6 hours following drug administration, measured in ml. The diuretic effect is expressed as percentage of the collected urine volume calculated on that of the group treated with the carrier.

TABLE IX

| Treatment | Average arterial pressure (mm Hg) | Diuretic effect % (n = 5) |
| --- | --- | --- |
| Carrier | 170 ± 7 | 100 |
| Amiloride.HNO$_3$ | 110 ± 5 | 215 |
| Amiloride | 158 ± 7 | 220 |

As it is evident from Table IX, the inhibiting effect of the Amiloride nitrate salt on the hypertension induced by L-NAME, is remarkable over that of Amiloride. As regards the vaso-relaxing activity, the two compounds show similar diuretic activity.

EXAMPLE 16

Studies of Acute Toxicity of the Sildenafil and Zaprinast Salts with Nitric Acid The two products have been administered in a suspension of carboxymethylcellulose 2%.

The acute toxicity of the above mentioned salts has been evaluated by oral administration of increasing doses of the compounds to groups of 10 rats each. Each group was administered of one dose.

The animals were kept under observation for 14 days. Lethality incidence and any toxic symptomatology was evaluated.

Even after administering of a 50 mg/Kg dose no sign of apparent toxicity was noticed. All the animals survived.

EXAMPLE 17

Studies of Gastric toxicity of the Sildenafil and Zarinast Salts with Nitric Acid in the Confront of that of the Precursors 5 groups of Sprague-Dawley male rats (n=10), were fasted for 24 hours. 4 groups were then respectively treated i.p. with Sildenafil, Zaprinast, and the relevant nitrate salts of said drugs. One group was not treated and was tha control group. 30 minutes later 1 ml of ethanol 50% in water was given by os to the animals.

One hour later the animals were sacrificed. The stomach was removed and the gastric tissue was macroscopically examined. This examination was carried out by a researcher unaware of the treatments to which the rats had been subjected prior of sacrifice. The presence of lesions was checked as described by Gretzer et al. (Br. J. Pharmacol. 123, 927, 1998).

The results are reported in Table X. In the Table the gastric toxicity given as % incidence is the number of rats in a group showing gastric lesions.

TABLE X

| Treatment | Drug as free base mg/Kg/i.p. | Gastric toxicity (% incidence) |
|---|---|---|
| Controls |  | 50 |
| Sildenafil | 10 | 100 |
| Sildenafil.HNO$_3$ | 10 | 20 |
| Zaprinast | 10 | 90 |
| Zaprinast.HNO$_3$ | 10 | 30 |

As noticed from the Table, in the groups of rats treated with Sildenafil or Zaprinast the gastric pathology was worsened with respect to the controls. The gastric toxicity of the corresponding nitrate salts of said drugs was lower than that of the control group.

EXAMPLE 18

Perhexiline Nitrate Preparation

Nitric acid 65% (0.75 ml) is added to a Perhexiline solution (3.02 g, 10.9 mmole) in acetonitrile and methanol (10 ml), cooled at 0° C.

The obtained solution is maintained under magnetic stirring at 0° C. for 30 minutes, then at room temperature for further 30 minutes. The solvent is evaporated under reduced pressure and the crude product is suspended in ethylic ether and then filtered.

The product (3.09 g) is obtained as white solid having melting point=151°–155° C.

Elemental Analysis:

|  | C | H | N |
|---|---|---|---|
| Calc. | 67.00% | 10.65% | 8.26% |
| Found | 67.05% | 10.79% | 8.40% |

EXAMPLE 19

Preparation of the Salt Apomorphine Nitrate

Silver nitrate (2.72 g, 16 mmoles) was added to a solution of apomorphine hydrochloride (5 g, 16 mmoles) in acetonitrile (70 ml), and the mixture was stirred in the dark and under a nitrogen atmosphere for 30 minutes. Silver chloride was filtered out and the solution was diluted with diethyl ether. A precipitate was formed that was filtered, washed with diethyl ether and dried under vacuum. 4,3 g were recovered

| C, H, N analysis | | | |
|---|---|---|---|
| calc. (%) | C 61.81 | H 5.49 | N 8.48 |
| found (%) | C 61.84 | H 5.45 | N 8.51 |

EXAMPLE 20

Preparation of the Salt Zaprinast Nitrate 0,5 ml of a solution nitric acid 65%/ acetonitrile (2,7 ml/7,3 ml) was added at 0° C. to a solution of Zaprinast (0,5 g, 1,84 mmoles) in acetonitrile (10 ml) and the obtained mixture was stirred in the dark and under a nitrogen atmosphere for 30 minutes. The solution was then diluted with diethyl ether and the formed precipitate filtered, washed with diethyl ether and dried under vacuum.( 0,4 g).

| C, H, N analysis | | | |
|---|---|---|---|
| calc. (%) | C 46.71 | H 4.22 | N 25.14 |
| found (%) | C 46.68 | H 4.26 | N 25.11 |

What is claimed is:

1. Nitrate salts of the compounds selected from the group consisting of:

1(2H)-phthalazinone hydrazone (Hydralazine); 6-(1-piperidinyl)-2,4-pyrimidinediamine 3-oxide (Minoxidil); 1-[[3-(4,7-dihydro-1-methyl-7-oxo-3-propyl-1H-pyrazol [4,3-d]pyrimidin-5-yl)-4-etoxyphenyl]sulphonyl]-4-methyl-piperazine (Sildenafil), and 2-(2-propyloxyphenyl)-8-azapurin-6-one (Zaprinast).

2. Salts according to claim 1, wherein the salts of said compounds contain at least one nitrate ion mole/compound mole.

3. Nitrate salts according to claim 1 of the following compounds:

Sildenafil or Zaprinast.

4. Pharmaceutical compositions of the nitrate salts according to claim 1 and a pharmaceutically acceptable carrier.

5. A method of treating hypertension, said method comprising administering to a patient in need thereof a hypertension treating effective amount of at least one compound of claim 1.

6. A method for treating cardiovascular disease, wherein said method comprises administering to a patient in need thereof a cardiovascular disease treating effective amount of at least one compound of claim 1.

7. A method for relaxing the cavernous artery or human cavernosum corpora, said method comprising administering to a patient in need thereof a cavernous artery or human cavernosum corpora relaxing effective amount of at least one compound of claim 1.

8. The method of claim 7, wherein the compound is sildenafil nitrate.

* * * * *

UNITED STATES PATENT AND TRADEMARK OFFICE
CERTIFICATE OF CORRECTION

PATENT NO. : 6,645,965 B1
DATED : November 11, 2003
INVENTOR(S) : Del Soldato

It is certified that error appears in the above-identified patent and that said Letters Patent is hereby corrected as shown below:

<u>Title page,</u>
Item [56], References Cited, FOREIGN PATENT DOCUMENTS, please add the omitted references cited:
-- GB    1 381 482A    01/1975
   WO   99 00361A    01/1999
   WO   98 21193A    05/1998 --
OTHER PUBLICATIONS, please add the omitted references cited:

-- "Ion Pair Extraction in Preparative Organic Chemistry", Chemica Scandinavica, Brändström et al., Vol. 23, No. 4, 1969, pages 1215-8. --

-- "Phase Solubility Technique in Studying the Formation of Complex Salts of Triamterene", Journal of Pharmaceutical Sciences, Dittert et al., Vol. 53, No. 11, 1964, pages 1325-8. --

Signed and Sealed this

Eleventh Day of May, 2004

JON W. DUDAS
*Acting Director of the United States Patent and Trademark Office*